United States Patent [19]

Lowe, III

[11] Patent Number: 4,891,375

[45] Date of Patent: Jan. 2, 1990

[54] ARYLPIPERAZINYL-ALKYLENE-PHENYL-HETEROCYCLIC COMPOUNDS

[75] Inventor: John A. Lowe, III, Stonington, Conn.

[73] Assignee: Pfizer Inc., New York, N.Y.

[21] Appl. No.: 143,909

[22] Filed: Jan. 13, 1988

Related U.S. Application Data

[63] Continuation-in-part of PCT US87/00340, Feb. 17, 1987.

[51] Int. Cl.$^4$ ................. C07D 417/10; C07D 403/14; C07D 403/04; A61K 31/495

[52] U.S. Cl. ................................ 514/252; 514/254; 544/284; 544/295; 544/363; 544/364; 544/366; 544/368; 544/369; 544/367; 544/370; 544/371

[58] Field of Search ............... 544/366, 284, 295, 363, 544/364, 367; 514/255, 252, 254

[56] References Cited

U.S. PATENT DOCUMENTS

| | | | |
|---|---|---|---|
| 2,927,924 | 3/1960 | Mills | 260/268 |
| 3,170,926 | 2/1965 | Ash et al. | 260/268 |
| 3,488,353 | 1/1970 | Archer | 260/268 |
| 3,649,631 | 3/1972 | Koppe et al. | 260/268 H |
| 3,729,474 | 4/1973 | Mentrup et al. | 260/268 BC |
| 3,975,525 | 8/1976 | Mentrup et al. | 424/250 |
| 4,619,929 | 10/1986 | Thieme et al. | 514/252 |

FOREIGN PATENT DOCUMENTS 948766  2/1964  United Kingdom .

OTHER PUBLICATIONS

Moore et al., J. Clin. Psychopharmacol, vol. 7, pp. 98–101 (1987).
Miller et al., Handbook of Drug Therapy, p. 528 (1979).
Braunwald et al., Harrison's Principles of Internal Medicine, pp. 2104–2105 (1987).

*Primary Examiner*—John M. Ford
*Attorney, Agent, or Firm*—Peter C. Richardson; Paul H. Ginsburg; Gezina Holtrust

[57] ABSTRACT

Arylpiperazinyl-alkylenephenyl-p-heterocyclic compounds, and the pharmaceutically acceptable acid addition salts thereof are neuroleptic agents. They are useful in the treatment of psychotic disorders.

13 Claims, No Drawings

ARYLPIPERAZINYL-ALKYLENE-PHENYL-HETEROCYCLIC COMPOUNDS

This application is a continuation-in-part of PCT/US 87/00340 filed Feb. 17, 1987.

BACKGROUND OF THE INVENTION

The invention relates to arylpiperazinyl-alkylenephenyl-p-heterocyclic compounds and the pharmaceutically acceptable acid addition salts thereof, pharmaceutical compositions containing these compounds and a method of using them.

Arylpiperazinyl-ethylphenyl compounds and their use in the treatment of psychiatric disorders are disclosed in U.S. Pat. Nos. 2,927,924 and 3,170,926. These prior art compounds may be substituted in the phenyl but heterocyclic substitution is not disclosed.

SUMMARY OF THE INVENTION

The compounds of the invention are arylpiperazinyl-alkylenephenyl-p-heterocyclic compounds of the formula

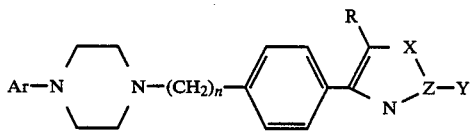

or a pharmaceutically acceptable acid addition salt thereof, wherein Ar is phenyl or 3-trifluoromethylphenyl; 3-cyanopyridyl; naphthyl, or a five or six membered aromatic heterocyclic ring said ring having one nitrogen, oxygen or sulfur, or two nitrogens one of which may be replaced by oxygen or sulfur, or said heterocyclic ring is condensed with benzo; each of said groups optionally substituted by one fluoro, chloro or trifluoromethyl; n is 2, 3 or 4; R is hydrogen or $(C_1-C_3)$alkyl; X is nitrogen, oxygen or sulfur, and Z-Y is C-H, C-OH, C-SH, C-$NH_2$, C-$(C_1-C_3)$alkyl, C$(C_1-C_3)$alkylamino, or nitrogen, with the proviso that when Z-Y is nitrogen, then X is not oxygen.

Specific compounds of the invention are those wherein n is 3 and Ar is benzisothiazole.

Preferred compounds of the invention are those wherein n is 2 and R is hydrogen, and those wherein n is 2 or 4, and Ar is naphthyl, a 5- or 6-membered aromatic heterocyclic ring condensed with benzo such as benzoisothiazolyl, or a 5- or 6-membered aromatic heterocyclic ring condensed with benzo, wherein said benzo is substituted by one of fluoro, chloro or trifluoromethyl.

Other preferred compounds are those wherein X is sulfur, and Y is amino.

Specific preferred compounds are
4-(4-(2-(4-(1-naphthyl)piperazinyl)ethyl)phenyl)-2-aminothiazole
4-(4-(2-(4-(3-trifluoromethylphenyl)piperazinyl)ethyl)-phenyl)-2-aminothiazole
4-(4-(2-(4-(1-naphthyl)piperazinyl)ethyl)phenyl)-2-amino-5-methylthiazole
4-(4-(2-(4-(3-trifluoromethylphenyl)piperazinyl)ethyl)-phenyl)-2-amino-5-methylthiazole
4-(4-(2-(4-(1-naphthyl)piperazinyl)ethyl)phenyl)thiazol-2-one
4-(4-(2-(4-(3-trifluoromethylphenyl)piperazinyl)ethyl)-phenyl)thiazol-2-one
4-(4-(2-(4-(3-benzisothiazolyl)piperazinyl)ethyl)-phenyl)-thiazol-2-one
4-(4-(4-(4-(3-benzisothiazolyl)piperazinyl)butyl)-phenyl)-2-aminothiazole
4-(4-(2-(4-(3-benzisothiazolyl)piperazinyl)ethyl)-phenyl)-2-methylthiazole
4-(4-(4-(4-(3-benzisothiazolyl)piperazinyl)butyl)-phenyl)-2-methylthiazole
4-(4-(4-(4-(3-benzisothiazolyl)piperazinyl)butyl)-phenyl)-thiazol-2-one
4-(4-(2-(3-(4-benzisothiazolyl)piperazinyl)ethyl)-phenyl)-thiadiazole
4-(4-(4-(4-(3-benzisothiazolyl)piperazinyl)butyl)-phenyl)-thiadiazole The present invention also relates to pharmaceutical compositions comprising a compound of formula I and a pharmaceutically acceptable carrier or diluent. Preferred compositions are those wherein the compound of formula I is a preferred compound or a specific preferred compound as described above.

This invention further comprises a method of treating a psychotic disorder by administering to a subject in need of treatment an effective amount of a compound of formula I. Preferred methods of treatment are those administering a preferred compound of formula I or a specific preferred compound as described above.

DETAILED DESCRIPTION OF THE INVENTION

The term "$(C_1-C_3)$alkyl" wherever used in the definition of R or Y denotes methyl, ethyl, propyl or isopropyl.

The five or six membered aromatic heterocyclic ring having one nitrogen, oxygen or sulfur, or two nitrogens one of which may be replaced by oxygen or sulfur includes furyl, pyrrolyl, pyrazolyl, imidazolyl, oxazolyl, thiazolyl, isothiazolyl, pyridyl and pyrimidyl. The substituent in the heterocyclic ring may be at any position, e.g. at the 5-position in 5-fluoropyrimidyl.

The heterocyclic ring may be condensed with benzo at two neighboring carbon atoms in the heterocyclic ring. Examples of such benzoheterocyclic groups are quinolyl, quinazolinyl, benzoxazolyl, benzimidazolyl, benzothiazolyl, and benzisothiazolyl.

The substitution by one fluoro, chloro or trifluoromethyl in naphthyl or benzoheterocyclyl is in the ring not attached to the piperazinyl group. An example of such substituted group is 6-fluoronaphthyl. The benzoheterocyclic group may be attached to the piperazinyl through the heterocyclic or through the benzo ring, for instance, the piperazinyl may be substituted by 8-quinolyl.

When Z-Y is not nitrogen, the heterocyclic group of the formula

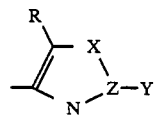

in formula I is imidazolyl when X is nitrogen, thiazolyl when X is sulfur, and oxazolyl when X is oxygen. When Z-Y is nitrogen and X is sulfur, the above heterocyclic group is thiadiazolyl; when Z-Y is nitrogen and X is nitrogen, then the above heterocyclic group is triazolyl.

The compounds of formula I are prepared by reacting piperazines of formula II with compounds of formula III as follows:

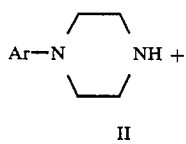

II

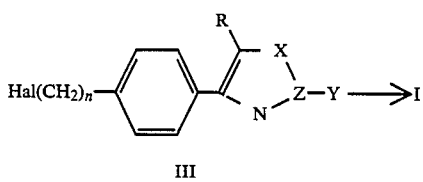

III wherein Hal is fluoro, chloro, bromo or iodo, and Ar, R, X and Z-Y are as defined above with reference to formula I. This coupling reaction is generally conducted in a polar solvent such as a lower alcohol, for instance ethanol, dimethylformamide or methylisobutylketone, and in the presence of a weak base such as a tertiary amine base, for instance triethylamine or diisopropylethylamine. Preferably, the reaction is in the further presence of a catalytic amount of sodium iodide, and a neutralizing agent for hydrochloride such as sodium carbonate or bicarbonate. The reaction is conducted at the reflux temperature of the solvent used. The piperazine derivatives of formula II may be prepared by methods known in the art. The compounds of formula III, wherein Z-Y and X are not both nitrogen, are prepared by reacting a compound of the formula

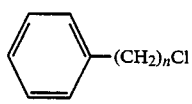

IV wherein n is 2, 3 or 4, with an acylchloride of the formula

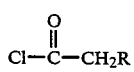

V wherein R is hydrogen or $(C_1-C_3)$alkyl, to form a compound of the formula

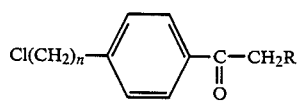

VI brominating to form a compound of the formula

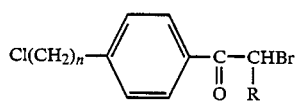

VII and reacting with (1) thiourea, urea or guanidine to form compounds (III) wherein X is sulfur, oxygen or nitrogen, respectively, and Z-Y is C-$NH_2$, (2) formamide or acetamide to form compounds (III) wherein X is nitrogen, and Z-Y is C-H or C-$CH_3$, respectively, (3) thioformamide or thioacetamide to form compounds (III) wherein X is sulfur, and Z-Y is C-H or C-$CH_3$, respectively, (4) thiocyanate or cyanate and hydrolyzing to form compounds (III) wherein X is sulfur or oxygen, respectively, and Z-Y is C-OH, (5) thiocyanate or cyanate and hydrosulfurizing with hydrogen sulfide to form compounds (III) wherein X is sulfur or oxygen, respectively, and Z-Y is C-SH (6) N-$(C_1-C_3)$alkylthiourea or N-$(C_1-C_3)$alkylurea to form compounds (III) wherein X is sulfur or oxygen, respectively, and Z-Y is C-$(C_1-C_3)$alkylamino, or (7) ammonium formate or ammonium acetate to form compounds (III) wherein X is oxygen, and Z-Y is C-H or C-$CH_3$, respectively.

The compounds (III) wherein X is nitrogen, and Z-Y is C-$(C_1-C_3)$alkylamino may be formed by alkylating the corresponding compound wherein Z-Y is C-$NH_2$. Conventional alkylation methods may be used such as reaction with a $(C_1-C_3)$alkyliodide in the presence of potassium carbonate and a solvent such as acetone.

The compounds of formula III wherein Z-Y is nitrogen, X is sulfur, and R is hydrogen, or $(C_1-C_3)$alkyl, may be prepared by reacting tosyl hydrazide with a compound of formula VI, followed by ring closure with thionyl chloride.

The above reaction to form compounds of formula VI is a Friedel-Crafts reaction which is generally conducted in the presence of a halohydrocarbon solvent such as ethylene dichloride, and a Lewis acid such as aluminum chloride, zinc chloride or tin chloride.

The above alpha-bromination to form compounds of the formula VII may be conducted with any brominating agent, such as bromine in acetic acid. The formed bromide (VII) is usually further reacted without isolation to form compounds (II) by cyclization. The above cyclization reactions (1) to (6) generally are conducted in a polar solvent such as ethanol or acetone under heating at reflux temperatures. The above cyclization reaction (7) is advantageously conducted with an excess of ammonium formate or acetate in formic acid or acetic acid, respectively, and heating to the boiling point of the mixture.

The compounds of formula III wherein X is nitrogen and Z-Y is C-OH or C-SH are prepared as follows. A compound of formula VII is reacted with hexamethylenetetramine in an organic solvent such as a chlorohydrocarbon, preferably chloroform, at about room temperature and the formed salt is hydrolyzed by conventional methods such as reaction with an acid, e.g. hydrochloric acid, in an alcohol to form a compound of the formula

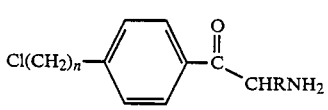

VIII in its acid addition salt form. The compound of formula VIII is reacted with chlorosulfonylisocyanate in an organic solvent such as a hydrocarbon solvent, e.g. toluene, in the presence of a trialkylamine such as triethylamine at about room temperature for about 1 to 5 hours, and then heated in a polar solvent such as aqueous dioxane with an acid such as acetic acid or hydrochloric acid or a mixture thereof for about 1 to 5 hours to form a compound (III) wherein X is nitrogen and Z-Y is C-OH.

The compound (III) wherein X is nitrogen and Z-Y is C-SH is formed by reacting a compound (VIII) with potassium thioisocyanate in water at reflux for about 30 minutes.

The compounds of formula III wherein Z-Y and X are both nitrogen and Hal is iodo may be prepared from the corresponding hydroxyl compound (IX) by stirring with tosyl chloride in pyridine at about 0° C., and then stirring at reflux with sodium iodide in acetone.

The hydroxyl compounds (IX) are formed from compounds of the formula X as follows:

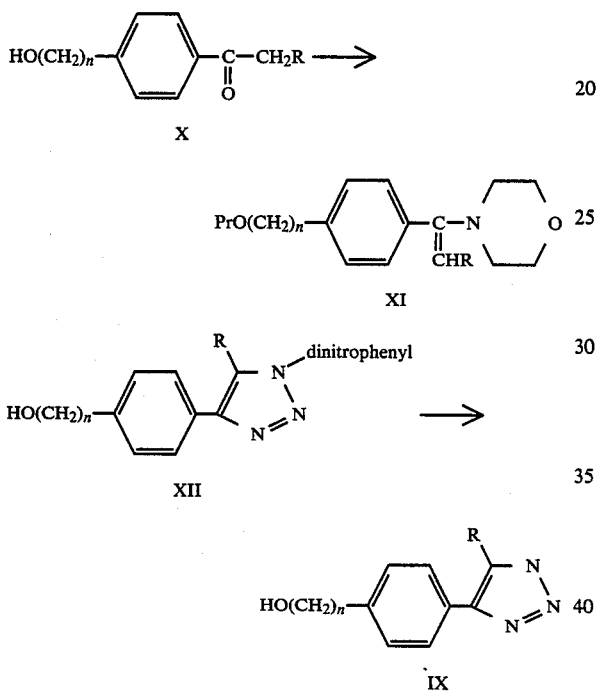

The compounds (X), wherein n is 2, 3 or 4, are first protected with a protecting group Pr, such as by reaction with dihydropyran with an acid such as p-toluenesulfonic acid in a solvent, e.g. benzene, and then reacted with morpholine and p-toluene sulfonic acid in a solvent such as benzene with removal of water to form compounds (XI). The compound of formula XI is refluxed with 2,4-dinitrophenylazide in chloroform for about three hours, the chloroform is removed and the reaction mixture taken up in hot aqueous acetic acid (1:1) to form compounds (XII). On reflux of compounds (XII) in an alcohol solvent in the presence of a base such as sodium hydroxide for more than 24 hours, compounds IX are formed.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzenesulfonic, and related acids.

The neuroleptic activity of the present compounds may be demonstrated by methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution. The rats are rated behaviorally according to the following scale at 5, 15, 25, 35 and 45 minutes after the apomorphin injection: 0=alert but not moving, 1=moving about the cage, 2=discontinuous sniffing behavior, 3=continuous sniffing with discontinuous oral movements, and 4=continuous licking and chewing movements.

The neuroleptic activity of the compounds of this invention makes them useful for, treating psychotic disorders in human subjects. For example, these compounds are useful for treating psychotic disorders of the schizophrenic types, and in particular the compounds are useful for removing or ameliorating such symptoms as anxiety, agitation, excessive agression, tension, and social or emotional withdrawal in psychotic patients.

A neuroleptic compound of formula I, or a pharmaceutically-acceptable salt thereof, can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes especially intravenous and intramuscular administration. Additionally, in a pharmaceutical composition comprising a compound of formula I, or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of a neuroleptic agent of this invention, the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When a neuroleptic agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from 5 to 500 mg, and preferably 50 to 100 mg, in single or divided doses, orally or parenterally. In some instances it may be necessary to use dosages outside these limits.

The following examples are provided solely for the purpose of further illustration.

EXAMPLE 1

A. 4-(2-Chloroethyl)-acetophenone

A solution was prepared by adding 7.11 ml (50 mmol) of acetyl chloride to a suspension of 7.34 g (55 mmol) of aluminum chloride in 35 ml of ethylene dichloride. This solution was added at room temperature to a solution of 6.58 ml (100 mmol) of phenethyl chloride in 10 ml of ethylene dichloride. The solution began to darken and give off hydrochloride and was stirred at room temperature for 25 minutes, then poured into ice and water. The layers were separated and the organic layer washed with 1N hydrochloride, saturated aqueous sodium bicarbonate solution, and brine, dried over sodium sulfate, and evaporated to an oil, which was used directly in the following reaction. NMR (CDCl$_3$): 2.16 (s, 3H), 2.68 (m, 2H), 3.30 (m, 2H), 6.85 (d, 2H), 7.45 (d, 2H). IR (cm$^{-1}$, neat): 1680 (C=O).

B. 4-(4-(2-Chloroethyl)phenyl)-2-aminothiazole hydrobromide

To a 50 ml round-bottomed flask equipped with nitrogen inlet were added 0.91 g (5 mmol) of 4-(2-chloroethyl)-acetophenone and 5 ml acetic acid. To the stirring solution was added 0.26 ml (5 mmol) of bromine dropwise over 2 minutes. The solution was stirred at room temperature for 1 hour, taken up in ethyl acetate, and washed with water, saturated aqueous sodium bicarbonate solution, and brine, dried, and evaporated to an oil. The oil was taken up in 25 ml acetone and treated with 0.38 g (5 mmol) of thiourea, and the reaction heated at reflux for 3 hours. The reaction was cooled to room temperature and allowed to stand for 2.5 hours, then the precipitate was collected, washed with a little acetone, and dried to give 0.81 g (51%) of a white solid, m.p. 193°–195° C.

C. 4-(4-(2-(4-(1-Naphthyl)piperazinyl)ethyl)phenyl)-2-aminothiazole

To a 35 ml round-bottomed flask equipped with condenser and N$_2$ inlet were added 3.19 g (10 mmol) of 4-(4-(2-chloroethyl)phenyl)-2-aminothiazole hydrobromide, 2.12 g (10 mmol) of N-(1-naphthyl)piperazine, 2.79 ml (20 mmol) of triethylamine, 1.06 g (10 mmol) of sodium carbonate, 2 mg of sodium iodide, and 25 ml of ethanol. The reaction was heated at reflux for 5 days, cooled, and the precipitate filtered, and washed with ethanol and water. The orange solid was chromatographed on silica gel using ethyl acetate/methylene chloride as eluent to give a white solid. The solid was taken up in ethyl acetate/methanol, ether saturated with HCl added, the precipitate filtered, washed with ether, and dried to give a white solid, 1.61 g (31%), m.p. 274°–277° C.

EXAMPLE 2

4-(4-(2-(4-(3-Trifluoromethylphenyl)piperazinyl)ethyl)phenyl)-2-aminothiazole To a 35 ml round-bottomed flask equipped with condenser and N$_2$ inlet were added 0.81 g (2.55 mmol) of 4-(4-(2-chloroethyl)phenyl)-2-aminothiazole hydrobromide, 0.68 g (2.55 mmol) of N-(3-trifluoromethylphenyl)piperazine hydrochloride, 1.06 ml (7.64 mmol) of triethylamine, 0.27 g (2.55 mmol) of sodium carbonate, 2 mg of sodium iodide, and 10 ml of ethanol. The reaction was heated at reflux for 8 days, cooled, and the precipitate filtered, and the reaction mixture taken up in ethyl acetate/water. The layers were separated, the ethyl acetate washed with brine, dried, and evaporated to give a white solid, which was triturated with ethyl acetate. The solid was taken up in ethyl acetate/methanol, ether saturated with HCl added, the precipitate filtered, washed with ether, and dried to give a white solid, 0.255 g (18%), m.p. 274°–277° C.

EXAMPLE 3

A. 4-(2-Chloroethyl)-propiophenone

A solution was prepared by adding 8.69 ml (50 mmol) of propionyl chloride to a suspension of 7.34 g (55 mmol) of aluminum chloride in 35 ml of ethylene dichloride. This solution was added at room temperature to a solution of 6.58 ml (100 mmol) of phenethyl chloride in 10 ml of ethylene dichloride. The solution began to darken and give off hydrochloride and was stirred at room temperature for 25 minutes, then poured into ice/water. The layers were separated and the organic layer washed with 1N hydrochloride, saturated aqueous sodium bicarbonate solution, and brine, dried over sodium sulfate, and evaporated to an oil, which was used directly in the following reaction. NMR (CDCl$_3$): 1.16 (t, 3H), 2.6–3.1 (m, 4H), 3.68 (m, 2H), 7.2 (d, 2H), 7.9 (d, 2H). IR (cm$^{-1}$, neat): 1690 (C=O).

B. 4-(4-(2-Chloroethyl)phenyl)-2-amino-5-methylthiazole hydrobromide

To a 50 ml round-bottomed flask equipped with N$_2$ inlet were added 0.98 g (5 mmol) of 4-(2-chloroethyl)-propiophenone and 5 ml acetic acid. To the stirring solution was added 0.26 ml (5 mmol) of bromine dropwise over 2 minutes. The solution was stirred at room temperature for 1 hour, taken up in ethyl acetate, and washed with water, saturated aqueous sodium bicarbonate solution, and brine, dried, and evaporated to an oil. The oil was taken up in 25 ml acetone and treated with 0.38 g (5 mmol) of thiourea, and the reaction heated at reflux for 3 hours. The reaction was cooled to room temperature and allowed to stand for 2.5 hours, then the precipitate was collected, washed with a little acetone, and dried to give 0.75 g (52%) of a white solid, m.p. 209°–211° C.

EXAMPLE 4

4-(4-(2-(4-(1-Naphthyl)piperazinyl)ethyl)phenyl)-2-amino-5-methylthiazole

To a 35 ml round-bottomed flask equipped with condenser and N$_2$ inlet were added 0.81 g (2.80 mmol) of 4-(4-(2-chloroethyl)phenyl)-2-amino-5-methylthiazole hydrobromide, 0.59 g (2.80 mmol) of N-(1-naphthyl)piperazine, 0.78 ml (5.60 mmol) of triethylamine, 0.30 g (2.80 mmol) of sodium carbonate, 2 mg of sodium iodide, and 10 ml of ethanol. The reaction was heated at reflux for 5 days, cooled, and the reaction taken up in ethyl acetate, washed with water and brine, dried over sodium sulfate, and evaporated to an oil. The oil was chromatographed on silica gel using ethyl acetate/methylene chloride as eluent to give a white solid. The solid was taken up in ethyl acetate/methanol, ether saturated with HCl added, the precipitate filtered, washed with ether, and dried to give a white solid, 0.82 g (54%), m.p. 160°–165° C.

EXAMPLE 5

4-(4-(2-(4-(3-Trifluoromethylphenyl)piperazinyl)ethyl)-phenyl)-2-amino-5-methylthiazole To a 35 ml round-bottomed flask equipped with condenser and $N_2$ inlet were added 0.75 g (2.59 mmol) of 4-(4-(2-chloroethyl)phenyl)-2-aminothiazole hydrobromide, 0.69 g (2.59 mmol) of N-(3-trifluoromethylphenyl)piperazine hydrochloride, 1.08 ml (7.78 mmol) of triethylamine, 0.27 g (2.59 mmol) of sodium carbonate, 5 mg of sodium iodide, and 9.5 ml of ethanol. The reaction was heated at reflux, cooled, and taken up in ethyl acetate/water. The layers were separated, the ethyl acetate washed with brine, dried, and evaporated to give an oil. The oil was chromatographed on silica gel using ethyl acetate as eluent to give an oil. The oil was taken up in ethyl acetate/methanol, ether saturated with HCl was added, the precipitate filtered, washed with ether, and dried to give a white solid, 0.72 g (50%), m.p. 110°–115° C.

EXAMPLE 6

A. 4-(4-(2-Chloroethyl)phenyl)-thiazol-2-one

To a 125 ml round-bottomed flask equipped with $N_2$ inlet were added 9.1 g (50 mmol) of 4-(2-chloroethyl)acetophenone and 25 ml acetic acid. To the stirred solution was added 2.58 ml (50 mmol) of bromine dropwise over 2 minutes. The reaction was stirred at room temperature for 30 minutes, taken up in ethyl acetate, washed with water, saturated aqueous sodium bicarbonate solution, and brine, dried over sodium sulfate, and evaporated to an oil. The oil was taken up in 250 ml of acetone, treated with 4.9 g (50 mmol) of potassium thiocyanate, and stirred at room temperature for 3 hours. The precipitate was filtered and the filtrate evaporated. The residue was taken up in ethyl acetate, washed with water and brine, dried over sodium sulfate, and evaporated to a solid. The solid was taken up in 100 ml of boiling ethanol and treated slowly with 83 ml of 1N HCl, then refluxed for 14 hours. The reaction was cooled and the precipitate filtered, washed with water, and dried to give 8.2 g (68%) of a white solid, m.p. 226°–229° C.

B. 4-(4-(2-(4-(3-Trifluoromethylphenyl)piperazinyl)ethyl)-phenyl)thiazol-2-one

To a 35 ml round-bottomed flask equipped with condenser and $N_2$ inlet were added 1.89 g (7.89 mmol) of 4-(4-(2-chloroethyl)phenyl)thiazol-2-one, 2.10 g (7.89 mmol) of N-(3-trifluoromethylphenyl)piperazine hydrochloride, 2.20 ml (15.8 mmol) of triethylamine, 0.84 g (7.89 mmol) of sodium carbonate, 2 mg of sodium iodide, and 20 ml of methylisobutylketone. The reaction was heated at reflux for 6 days, cooled, and evaporated. The residue was taken up in ethyl acetate/water, the layers separated, and the ethyl acetate layer washed with brine, dried over sodium sulfate, and evaporated. The residue was chromatographed on silica gel using ethyl acetate/methylene chloride as eluent. The product fractions were evaporated, and the residue triturated with ether, taken up in hot ethyl acetate, treated with ethyl acetate saturated with hydrochloride, precipitated with ether, filtered, washed with ether, and dried to give 0.787 g (20%) of a white solid, m.p. 285°–287° C.

EXAMPLE 7

4-(4-(2-(4-(1-Naphthyl)piperazinyl)ethyl)phenyl)-thiazol-2-one

To a 35 ml round-bottomed flask equipped with condenser and $N_2$ inlet were added 1.40 g (5.84 mmol) of 4-(4-(2-chloroethyl)phenyl)thiazol-2-one, 1.24 g (5.84 mmol) of N-(1-naphthyl)piperazine, 0.81 ml (5.84 mmol) of triethylamine, 0.62 g (5.84 mmol) of sodium carbonate, 2 mg of sodium iodide, and 12 ml of methylisobutylketone. The reaction was heated at reflux for 5 days, cooled, and evaporated. The residue was taken up in ethyl acetate/water, the layers separated, and the ethyl acetate layer washed with brine, dried over sodium sulfate, and evaporated. The residue was chromatographed on silica gel using ethyl acetate/methylene chloride as eluent. The product fractions were evaporated, and the residue taken up in hot methylene chloride/methanol, treated with ethyl acetate saturated with hydrochloride, precipitated with ether, filtered, washed with ether, and dried to give 0.523 g (18%) of a white solid, m.p. 307°–309° C.

EXAMPLE 8

4-(4-(2-(4-(3-Benzisothiazolyl)piperazinyl)ethyl)-phenyl)-2-aminothiazole

To a 50 ml round-bottomed flask equipped with condenser and $N_2$ inlet were added 2.4 g (7.53 mmol) of 4-(4-(2-chloroethyl)phenyl)-2-aminothiazole hydrobromide, 1.65 g (7.53 mmol) of N-(3-benzisothiazolyl) piperazine (prepared according to the method of U.S. Pat. No. 4,411,901), 1.3 ml (7.53 mmol) of diisopropylethylamine, 1.6 g (15.1 mmol) of sodium carbonate, 2 mg of sodium iodide, and 25 ml of methylisobutylketone. The reaction was heated at reflux for 5 days, cooled, evaporated, and taken up in ethyl acetate/water. The ethyl acetate layer was separated, washed with water and brine, dried over sodium sulfate, and evaporated. The residue was chromatographed on silica gel using ethyl acetate as eluent to give a solid. The solid was taken up in hot ethyl acetate, precipitated by addition of hydrochloride gas, the precipitate filtered, washed with ether, and dried to give a beige solid, 1.536 g (38%), m.p. >300° C. (dec.). NMR (DMSO-d6): 3.2–3.8 (m, 10H), 4.1 (m, 2H), 7.25 (s, 1H), 7.4–8.2 (m, 8H), 11.5 (bs, 2H).

EXAMPLE 9

4-(4-(2-(4-(8-Quinolyl)piperazinyl)ethyl)phenyl)-2-aminothiazole

To a 35 ml round-bottomed flask equipped with condenser and $N_2$ inlet were added 0.746 g (2.34 mmol) of 4-(4-(2-chloroethyl)phenyl-2-aminothiazole hydrobromide, 0.50 g (2.34 mmol) of N-(8-quinolyl)piperazine (prepared from 8-aminoquinoline by reaction with diethanolamine in hydrobromide at 200° C.), 0.621 g (5.86 mmol) of sodium carbonate, 50 mg of sodium iodide, and 10 ml of ethanol. The reaction was heated at reflux for 25 hours, cooled, and the reaction mixture taken up in ethyl acetate/water. The layers were separated, the ethyl acetate layer dried and evaporated. The residue was chromatographed on silica gel using chloroform/methanol as eluent and the product fractions combined in methanol and precipitated with a solution of hydrochloride in ether. The precipitate was stirred with ether/methanol to afford a crystalline solid, m.p. >225° C., 277 mg (27%). NMR (free base in CDCl₃): 2.8 (m, 8H), 3.5 (m, 4H), 7.0–8.2 (m, 11H).

EXAMPLE 10

A. 4-(4-(2-Chloroethyl)phenyl)-2-methylaminothiazolehydrobromide

To a 500 ml round-bottomed flask equipped with $N_2$ inlet and condenser were added 32.7 g (0.125 mol) of bromomethyl(p-chloroethyl)phenyl ketone, 11.3 g (0.125 mol) N-methylthiourea, 250 ml acetone and 5 ml methanol. The reaction was refluxed for 14 hours, cooled, and evaporated to a gum. The gum was extracted with boiling acetone, and the extracts cooled to give a solid, which was filtered. The filtrate was evaporated and cooled further to give a white solid, m.p. 103°–107° C., 6.6 g (16%). NMR (DMSO-d6): 3.10 (t, 2H), 3.10 (s, 3H), 3.93 (t, 2H), 7.20 (s, 1H), 7.3–7.8 (m, 4H).

B. 4-(4-(2-(4-(1-Naphthyl)piperazinyl)ethyl)phenyl)-2-methylaminothiazole

To a 125 ml round-bottomed flask equipped with condenser and $N_2$ inlet were added 2.50 g (7.5 mmol) of 4-(4-(2-chloroethyl)phenyl)-2-methylaminothiazole hydrobromide, 1.59 g (7.5 mmol) of N-(1-naphthyl)piperazine, 1.31 ml (7.5 mmol) of diisopropylethylamine, 1.59 g (15 mmol) of sodium carbonate, 5 mg of sodium iodide, and 50 ml of methylisobutylketone. The reaction was heated at reflux for 4 days, cooled, and the precipitate filtered, and the filtrate evaporated. The residue was taken up in methylene chloride and chromatographed on silica gel using methylene chloride/ethyl acetate as eluent to give an oil. The oil was taken up in methylene chloride, precipitated by addition of methylene chloride saturated with hydrochloride, and the precipitate filtered, washed with ether, and dried to give a white solid, m.p. 272°–273° C., 2.37 g (63%).

EXAMPLE 11

4-(4-(2-(4-(3-Trifluoromethylphenyl)piperazinyl)ethyl)phenyl)-2-methylaminothiazole To a 125 ml round-bottomed flask equipped with condenser and $N_2$ inlet were added 2.50 g (7.5 mmol) of 4-(4-(2-chloroethyl)phenyl)-2-methylaminothiazole hydrobromide, 2.0 g (7.5 mmol) of N-(3-trifluoromethylphenyl)pperazine hydrochloride, 2.62 ml (15.0 mmol) of diisopropylethylamine, 1.59 g (15.0 mmol) of sodium carbonate, 5 mg of sodium iodide, and 50 ml of methylisobutylketone. The reaction was heated at reflux for 3.5 days, cooled, and the precipitate filtered, and the filtrate evaporated. The residue was chromatographed on silica gel using methylene chloride/ethyl acetate and ethyl acetate as eluents. The product fractions were concentrated, taken up in methylene chloride/methanol, precipitated by addition of ethyl acetate saturated with hydrochloride, and the precipitate filtered, washed with acetone/ether, and dried to give a white solid, m.p. 190°–195° C. Further material from the precipitate formed in the reaction gave a total yield of 1.16 g (30%).

EXAMPLE 12

A. 4-(4-(2-Chloroethyl)phenyl)-2-methylthiazole hydrobromide

To a 500 ml round-bottomed flask equipped with $N_2$ inlet and condenser were added 32.7 g (0.125 mol) of bromomethyl(p-chloroethyl)phenyl ketone, 9.39 g (0.125 mol) thioacetamide, and 250 ml acetone. The reaction was refluxed for 16 hours, cooled, and the precipitate which formed on cooling filtered, washed with acetone and ether, and dried to afford a white solid, m.p. 85°–89° C., 13.25 g (33%).

B. 4-(4-(2-(4-(1-Naphthyl)piperazinyl)ethyl)phenyl)-2-methylthiazole

To a 125 ml round-bottomed flask equipped with condenser and $N_2$ inlet were added 2.39 g (7.5 mmol) of 4-(4-(2-chloroethyl)phenyl)-2-methylthiazole hydrobromide, 1.59 g (7.5 mmol) of N-(1-naphthyl)piperazine, 1.31 ml (7.5 mmol) of diisopropylethylamine, 1.59 g (15 mmol) of sodium carbonate, 5 mg of sodium iodide, and 50 ml of methylisobutylketone. The reaction was heated at reflux for 5 days, cooled, and the precipitate filtered. The solid was taken up in methylene chloride, washed with sodium bicarbonate, dried over sodium sulfate, treated with methylene chloride saturated with hydrochloride, evaporated, and the residue triturated with ether to afford a white solid, m.p. 305°–307° C., 1.76 g (48%).

EXAMPLE 13

4-(4-(2-(4-(3-Trifluoromethylphenyl)piperazinyl)ethyl)phenyl)-2-methylthiazole To a 125 ml round-bottomed flask equipped with condenser and $N_2$ inlet were added 2.39 g (7.5 mmol) of 4-(4-(2-chloroethyl)phenyl)-2-methylthiazole hydrobromide, 2.0 g (7.5 mmol) of N-(3-trifluoromethylphenyl)piperazine hydrochloride, 2.62 ml (15.0 mmol) of diisopropylethylamine, 1.59 g (15.0 mmol) of sodium carbonate, 5 mg of sodium iodide, and 50 ml of methylisobutylketone. The reaction was heated at reflux for 4.5 days, filtered hot to remove inorganic material, cooled, and the precipitate filtered and washed with ether and ethyl acetate. The solid was taken up in methylene chloride, hydrochloride gas bubbled through to precipitate the salt, and the resulting solid filtered, washed with methylene chloride, and dried to give a solid, m.p. 170°–175° C., 1.93 g (51%).

EXAMPLE 14

A. 4-(4-(4-Chlorobutyl)phenyl)-2-aminothiazole hydrobromide

To a 500 ml round-bottomed flask equipped with $N_2$ inlet and condenser were added 25 g (86 mmol) of bromomethyl(p-chlorobutyl)phenyl ketone, 6.55 g (86 mol) thiourea, and 200 ml acetone. The reaction was refluxed for 1 hour 15 minutes, cooled, and the precipitate filtered, washed with acetone, and dried to a white solid, m.p. 208°–211° C., 23.77 g (80%).

B. 4-(4-(4-(4-(3-Trifluoromethylphenyl)piperazinyl)butyl)phenyl)-2-aminothiazole To a 125 ml round-bottomed flask equipped with condenser and $N_2$ inlet were added 2.61 g (7.5 mmol) of 4-(4-(4-chlorobutyl)phenyl)-2-aminothiazole hydrobromide, 2.0 g (7.5 mmol) of N-(3-trifluoromethylphenyl)-piperazine hydrochloride, 2.62 ml (15.0 mmol) of diisopropylethylamine, 1.59 g (15.0 mmol) of sodium carbonate, 5 mg of sodium iodide, and 50 ml of methylisobutylketone. The reaction was heated at reflux for 3.5 days, cooled, and the precipitate filtered, and the filtrate evaporated. The residue was chromatographed on silica gel using methylene chloride/ethyl acetate and ethyl acetate as eluents. The product fractions were concentrated, taken up in methylene chloride/methanol, precipitated by addition of ethyl acetate saturated with hydrochloride, evaporated, and the residue triturated with ether/ethyl acetate to afford a white solid, m.p. 174°–179° C., 0.87 g (23%).

EXAMPLE 15

4-(4-(4-(4-(1-Naphthyl)piperazinyl)butyl)phenyl)-2-aminothiazole

To a 125 ml round-bottomed flask equipped with condenser and N$_2$ inlet were added 2.61 g (7.5 mmol) of 4-(4-(4-chlorobutyl)phenyl)-2-methylaminothiazole hydrobromide, 1.59 g (7.5 mmol) of N-(1-naphthyl)piperazine, 1.31 ml (7.5 mmol) of diisopropyethylamine, 1.59 g (15 mmol) of sodium carbonate, 5 mg of sodium iodide, and 50 ml of methylisobutylketone. The reaction was heated at reflux for 4.5 days, cooled, and the precipitate filtered, and the filtrate evaporated. The residue was taken up in methylene chloride and chromatographed on silica gel using methylene chloride/ethyl acetate as eluent to give an oil. The oil was taken up in ethyl acetate, precipitated by addition of ethyl acetate saturated with hydrochloride, and the precipitate filtered, washed with ethyl acetate, and dried to give a white solid, m.p. 242°–245° C., 1.67 g (43%).

EXAMPLE 16

A. 4-(2-chloroethyl)-acetophenone tosylhydrazone

To a 500 ml round-bottomed flask equipped with condenser and N$_2$ inlet were added 32 g (176 mmol) of 4-(2-chloroethyl)acetophenone, 32.7 g (176 mmol) tosyl hydrazide, and 250 ml ethanol. The reaction was reflused for 3 hours, cooled, and evaporated. The product crystallized on standing in ether to give a solid, m.p. 122°–125° C., 20.3 g (33%).

B. 4-(2-chloroethyl)-phenyl-1,2,3-thiadiazole

To a 100 ml round-bottomed flask equipped with N$_2$ inlet were added 1.3 g (3.71 mmol) of the above tosyl hydrazone and 3.0 ml (41.1 mmol) thionyl chloride. The reaction gave a crystalline precipitate on standing at room temperature for 1 hour, which was collected with hexane to give a solid, m.p. 80°–81° C., 0.33 g (39%). The remainder of the reaction was chromatographed using methylene chloride to afford an additional 0.33 g of product.

C. 4-(4-(2-(4-(3-Benzisothiazolyl)piperazinyl)ethyl)-phenyl)-1,2,3-thiadiazole

To a 100 ml round-bottomed flask equipped with condenser and N$_2$ inlet were added 0.90 g (4 mmol) 4-(4-(2-chloroethyl)phenyl)-1,2,3-thiadiazole, 0.88 g (4 mmol) N-benzisothiazolylpiperazine, 0.84 g (8 mmol) sodium carbonate, 1.39 ml (8 mmol) diisopropylethyl amine, 2 mg sodium iodide, and 40 ml methylisobutyl ketone. The reaction was refluxed 2.5 days, cooled, filtered, and the filtrate evaporated. The residue was chromatographed on silica gel using ethyl acetate/methylene chloride as eluent to afford an oil, which was taken up in methylene chloride and precipitated by addition of ether saturated with HCl. The solid was filtered, washed with ether, dried under nitrogen, washed with acetone, and dried to afford a white solid, m.p. 257°–259° C., 1.02 g (57.4%).

EXAMPLE 17

A. 4-(4-(4-Chlorobutyl)phenyl)-1,2,3-thiadiazole

To a 125 ml round-bottomed flask equipped with condenser and N$_2$ inlet were added 6.25 g (29.65 mmol) p-(4-chlorobutyl)acetophenone, 5.57 g (29.65 mmol) tosylhydrazine, and 50 ml ethanol. The reaction was refluxed 3.5 hours, cooled, and evaporated. The residue was taken up in 23.4 ml (326 mmol) thionyl chloride and stirred at room temperature for 3 hours. The reaction mixture was evaporated and the residue chromatographed on silica gel using hexane/methylene chloride as eluent to afford an oil, 6.1 g (81.5%). NMR (CDCl$_3$): 1.84 (m, 4H), 2.73 (m, 2H), 3.58 (m, 2H), 7.3 and 7.95 (m, 4H), 8.59 (s, 1H).

B. 4-(4-(4-(4-(3-Benzisothiazolyl)piperazinyl)butyl)-phenyl)-1,2,3-thiadiazole

To a 65 ml round-bottom flask equipped with condenser and N$_2$ inlet were added 1.43 g (5.66 mmol) 4-(4-(4-chlorobutyl)phenyl)-1,2,3-thiadiazole, 0.90 g (4.11 mmol) N-benzisothiazolylpiperazine, 1.43 ml (8.22 mmol)diisopropylethyl amine, 0.87 g (8.22 mmol) sodium carbonate, 2 mg sodium iodide, and 30 ml methylisobutyl ketone. The reaction was refluxed for 24 hours, cooled, filtered, and the filtrate evaporated. The residue was chromatographed on silica gel using ethyl acetate/methylene chloride as eluent to give an oil, which was taken up in ethyl acetate and precipitated by addition of ethyl acetate saturated with HCl. The solid was filtered, washed with ethyl acetate, and dried to afford 1.70 g (87.6%), m.p. 246°–247° C., white solid.

EXAMPLE 18

A. 6-Fluoro-1-naphthoic acid

To a 1 liter round-bottomed flask equipped with condenser and N$_2$ inlet were added 345 ml (3.68 mol) of fluorobenzene and 48 g (0.428 mol) of furoic acid. To the stirring suspension was added in portions 120 g (0.899 mmol of aluminum chloride. The reaction mixture was stirred at 95° C. for 16 hours and then quenched by addition to ice/water/1N HCl. After stirring 1 hour, the aqueous layer was decanted, and benzene and a saturated aqueous solution of sodium bicarbonate were added. After stirring 1 hour, the layers were separated, the aqueous layer washed with benzene, acidified, and extracted into ethyl acetate. The ethyl acetate layer was washed with water and brine, dried over sodium sulfate, and evaporated to a solid. The solid was triturated with isopropyl ether to give 5.0 g (6.1%) of a white solid, NMR (DMSO-d$_6$): 7.0–8.0 (m, 5H), 8.6 (m, 1H).

B. 6-Fluoro-1-amino-naphthalene

To a 125 ml round-bottomed flask equipped with condenser, addition funnel, and N$_2$ inlet were added 5.0 g (26.3 mmol) of 6-fluoro-1-naphthoic acid and 50 ml acetone. To the stirring suspension were added dropwise 6.25 ml (28.9 mmol) of diphenyl phosphoryl azide and 4 ml (28.9 mmol) of triethylamine. The reaction was refluxed 1 hour, poured into water/ethyl acetate, and filtered. The filtrate was washed with water and brine, dried over sodium sulfate, and evaporated. The residue was further treated with HCl to form the hydrochloride salt and then liberated with sodium hydroxide to afford the free base as an oil, 1.0 g. (24%).

C. 1-Benzyl-4-(6-fluoronaphthyl)-piperazine

To a 125 ml round-bottomed flask equipped with condenser and $N_2$ inlet were added 1.0 g (6.21 mmol) of 6-fluoro-1-amino naphthalene, 1.8 g (7.76 mmol) of N-benzyl bis(2-chloroethyl)amine, 3.3 ml (19.2 mmol) of diisopropylethylamine, and 50 ml isopropanol. The reaction was refluxed 24 hours, cooled, and evaporaated to an oil. The oil was taken up in ethyl acetate, washed with waterand brine, dried over sodium sulfate, and evaporated to an oil. The oil was chromatographed on silica gel using methylene chloride as eluent to afford 1.5 g (75.5%) of an oil.

D. N-(1-(6-fluoro)naphthyl)piperazine

To a 125 ml round-bottomed flask equipped with $N_2$ inlet were added 1.5 g (4.69 mmol) of 1-benzyl-4-(6-fluoronaphthyl)-piperazine, 1.2 ml (31.3 mmol) of formic acid, 3.0 g 5% palladium on carbon, and 50 ml ethanol. The reaction was stirred at room temperature for 16 hours, the catalyst filtered under $N_2$, and the solvent evaporated. The oil (0.420 g, 39%) was used directly in the following step.

E. 4-(4-(2-(4-(6-Fluoronaphth-1-yl)piperazinyl)ethyl)-phenyl)-2-aminothiazole To a 100 ml round-bottomed flask equipped with condenser and $N_2$ inlet were added 500 mg (2.17 mmol) N-(1-(6-fluoro)naphthyl)piperazine, 700 mg (2.17 mmol) -(4-(2-chloroethyl)phenyl)-2-aminothiazole hydrobromide, 460 mg (4.35 mmol) sodium carbonate, 0.37 ml (2.17 mmol) diisopropylethylamine, and 25 ml methylisobutylketone. The reaction was refluxed 24 hours, cooled, and evaporated. The residue was taken up in ethyl acetate, washed with water and brine, dried over sodium sulfate, and evaporated. The residue was chromatographed on silica gel using methylene chloride/ethyl acetate as eluent. The product fractions were combined, dissolved in methylene chloride/methanol, treated with ethyl acetate saturated with HCl, and the precipitate collected and dried to give a white solid, m.p. 220°–225° C., 297 mg (25.3%). NMR (DMSO-$d_6$): 3.3–3.6 (m, 10H), 3.7–3.8 (m, 2H), 7.2–8.3 (m, 11H), 11.6 (bs, 2H).

EXAMPLE 19

4-(4-(2-(4-(6-Fluoronaphth-1-yl)piperazinyl)ethyl)-phenyl)-thiazol-2-one

To a 100 ml round-bottomed flask equipped with condenser and $N_2$ inlet were added 750 mg (3.27 mmol) N-(1-(6-fluoro)naphthyl)piperazine, 1.05 g (3.27 mmol) 4-(4-(2-chloroethyl)phenyl)-thiazol-2-one hydrobromide, 700 mg (6.52 mmol) sodium carbonate, 0.60 ml (3.27 mmol) diisopropylethylamine, 2 mg sodium iodide, and 35 ml methylisobutylketone. The reaction mixture was refluxed 24 hours, cooled, and evaporated. The residue was taken up in ethyl acetate, washed with water and brine, dried over sodium sulfate, and evaporated. The residue was chromatographed on silica gel using methylene chloride/ethyl acetate as eluent. The product fractions were collected to give a solid, 281 mg (19%), m.p. 228–270° C. NMR (DMSO-$d_6$): 2.7–3.3 (m, 12H), 6.80 (s, 1H), 7.1–8.2 (10H), 11.8 (bs, 1H).

EXAMPLE 20

4-(4-(2-(4-(6-Chloronaphth-1-yl)piperazinyl)ethyl)-phenyl)-2-aminothiazole

To a 100 ml round-bottomed flask equipped with condenser and $N_2$ inlet were added 440 mg (1.55 mmol) N-(1-(6-chloro)naphthyl)piperazine (prepared in analogy to the fluoro compound in Example 19D), 500 mg (1.55 mmol) 4-(4-(2-chloroethyl)phenyl)-2-aminothiazole hydrobromide, 500 mg (4.66 mmol) sodium carbonate 2 mg sodium iodide, and 30 ml methylisobutylketone. The reaction was refluxed 24 hours, cooled, and evaporated. The residue was taken up in ethyl acetate, washed with water and brine, dried over sodium sulfate, and evaporated. The residue was taken up in ether/methylene chloride and precipitated by addition of HCl gas. The precipitate was filtered, washed with ether, and dried to give a solid, 425 mg (42.5 %), m.p. 210–215° C. NMR (DMSO-$d_6$): 3.0–4.0 (m, 12H), 7.2–8.2 (m, 11H), 11.1 (bs, 2H).

EXAMPLE 21

4-(4-(2-(4-(3-Benzisothiazolyl)piperazinyl)ethyl)-thiazol-2-one

To a 100 ml round-bottomed flask equipped with condenser and $N_2$ inlet were added 1.0 g (4.57 mmol) 3-piperazinyl-benzisothiazole, 1.46 g (4.57 mmol) 4-(4-(2-chloroethyl)phenyl)thiazol-2-one hydrobromide, 970 mg (9.13 mmol) sodium carbonate, 600 mg (4.57 mmol) diisopropylethylamine, 2 mg sodium iodide, and 35 ml methylisobutylketone. The reaction was refluxed 24 hours, cooled, and evaporated. The residue was taken up in ethyl acetate, washed with water and brine, dried over sodium sulfate, and evaporated. The residue was chromatographed on silica gel using methylene chloride/ethyl acetate as eluent. The product fractions were dissolved in methylene chloride/ethyl acetate and precipitated with HCl gas. The precipitate was filtered to give a solid, m.p. 190° C., 455 mg (21.9%).

EXAMPLE 22

4-(4-(4-(4-(3-Benzisothiazolyl)piperazinyl)butyl)-phenyl)-2-aminothiazole

To a 100 ml round-bottomed flask equipped with condenser and $N_2$ inlet were added 1.22 g (3.52 mmol) (4-(4-(4-chlorobutyl)phenyl)-2-aminothiazole, 0.90 g (3.52 mmol) 3-piperazinyl-benzisothiazole, 1.84 ml (10.57 mmol) diisopropylethylamine, 0.75 g (7.04 mmol) sodium carbonate, 2 mg sodium iodide, and 35 ml methylisobutylketone. The reaction mixture was refluxed 6 days, cooled, and evaporated. The residue was chromatographed on silica gel using methylene chloride-/ethyl acetate as eluent, and the product fractions dissolved in methylene chloride/methanol and precipitated by addition of methylene chloride saturated with HCl. The precipitate was filtered and dried to give a solid, 242 mg (13%), m.p. 258–261° C. NMR (DMSO-$d_6$): 1.6–1.8 (m, 4H), 2.7 (t, 2H), 3.2–3.6 (m, 8H), 4.1 (m, 2H), 7.20 (s, 1H), 7.3–8.2 (m, 8H).

EXAMPLE 23
4-(4-(2-(4-(3-Benzisothiazolyl)piperazinyl)ethyl)-phenyl)-2-methylthiazole To a 100 ml round-bottomed flask equipped with condenser and $N_2$ inlet were added 0.95 g (4.34 mmol) 3-piperazinyl-benzisothiazole, 1.38 g (4.34 mmol) 4-(4-(2-chloroethyl)phenyl)-thiazol-2-one hydrobromide, 1.51 ml (8.68 mmol) diisopropylethylamine, 0.92 g (8.68 mmol) sodium carbonate, 2 mg. sodium iodide, and 40 ml methylisobutylketone. The reaction was refluxed 6 days, cooled, and evaporated. The residue was chromatographed on silica gel using methylene chloride-/ethyl acetate as eluent and the product fractions taken up in ether/methylene chloride and precipitated by addition of ether saturated with HCl. The precipitate was filtered and dried to give a solid, m.p. 135–140° C., 1.09 g (51%). NMR (DMSO-$d_6$) 2.74 (s, 3H), 3.1–3.7 (m, 10H), 4.1 (d, 2h), 7.3–8.2 (m, 9H).

EXAMPLE 24
4-(4-(2-(4-(Naphth-1-yl)piperazinyl)ethyl)phenyl)-1,2,3-thiadiazole 1,2,3-thiadiazole To a 100 ml round-bottomed flask equipped with condenser and $N_2$ inlet were added 0.64 g (2.83 mmol) (4-(4-2-chloroethyl)phenyl)-1,2,3-thiadiazole, 0.60 g (2.83 mmol) N-(1-naphthyl)piperazine, 0.49 ml (2.83 mmol) diisopropylethylamine, 0.60 g (5.66 mmol) sodium carbonate, 2 mg sodium iodide, and 20 ml methylisobutylketone. The reaction was refluxed 4 days, cooled, and evaporated. The residue was taken up in ethyl acetate, washed with water and brine, dried over sodium sulfate, and evaporated. The residue was chromatographed on silica gel using methylene chloride-/ethyl acetate as eluent and the product fractions dissolved in ethyl acetate and precipitated with ethyl acetate saturated with HCl. The precipitate was filtered and dried to give a solid, 0.62 g (50%), m.p. 286–289° C. NMR (DMSO-$d_6$ and TFA): 3.6 (m, 2H), 3.9 (m, 2H), 4.4–4.7 (m, 8H), 7.5–8.2 (m, 11H), 9.42 (s, 1H).

EXAMPLE 25
4-(4-(4-(4-(3-Cyanopyridin-2-yl)piperazinyl)butyl)-phenyl)-2-amino-thiazole To a 100 ml round-bottomed flask equipped with condenser and $N_2$ inlet were added 2.37 g (6.81 mmol) 4-(4-(4-chlorobutyl)phenyl)-2-aminothiazole hydrobromide, 1.28 g (6.81 mmol) 3-cyano-2-piperazinylpyridine, 2.38 ml (13.6 mmol) diisopropylethylamine, 1.44 g (13.6 mmol) sodium carbonate, 2 mg sodium iodide, and 40 ml methylisobutylketone. The reaction was refluxed 4 days, cooled, and evaporated. The residue was triturated with ethyl acetate and the resulting solid chromatographed on silica gel with methylene chloride-/ethyl acetate. The product fractions were dissolved in ethyl acetate, precipitated with ethyl acetate saturated with HCl, and the precipitate filtered and dried to give a solid, 1.84 g (55%), m.p. 155–162° C. NMR (DMSO-$d_6$) 1.6–1.8 (m, 4H), 2.67 (t, 2H), 3.1–4.4 (m, 10H), 7.34 (s, 1H), 7.1–8.5 (m, 7H), 11.3 (bs, 2H).

EXAMPLE 26
A. 4-Chlorobutylacetophenone

To a 250 ml round-bottomed flask were added 5.0 g (29.65 mmol) 4-chlorophenylbutane and 10 ml 1,2-dichloroethane. To the stirred solution was added a solution of 4.35 g (32.62 mmol) aluminum chloride and 4.22 ml (59.31 mmol) acetyl chloride in 50 ml 1,2-dichloroethane. The solution evolved HCl as it was stirred at room temperature for 1 hour. It was then poured into water, the layers were separated, and the organic layer was washed with 1N HCl, aqueous sodium bicarbonate solution, and brine, dried over sodium sulfate, and evaporated to an oil, 6.7 g (>100%). NMR (CDCl$_3$): 1.76 (m, 4H), 2.54 (m, 3H), 2.66 (m, 2H), 3.50 (m, 2H), 7.2 and 7.85 (m, 4H). IR (cm.$^{-1}$, neat): 1678 (C=O).

B. 4-(4-Chlorobutyl)phenyl-2-methylthiazole hydrobromide

The above oil was added to a 100 ml round-bottomed flask equipped with $N_2$ inlet along with 15 ml acetic acid. Bromine (1.53 ml, 29.65 mmol) was added dropwise and the solution stirred at room temperature for 15 minutes (decolorizes in about 7 minutes). The solution was carefully taken up in ethyl acetate, washed with water, aqueous sodium bicarbonate solution, and brine, dried over sodium sulfate, and evaporated to an oil, 8.9 g (about 100 % yield).

The oil was dissolved in 70 ml acetone, treated with 2.23 g (29.65 mmol) thioacetamide and refluxed for 15 hours. The reaction was cooled, evaporated to 10 ml volume to afford a precipitate. After filtration, the precipitate was washed with 10 ml acetone, then thoroughly washed with ether, and dried to a white solid, m.p. 128–129° C., 6.8 g (66.2%).

C. 4-(4-(4-(4-(3-Benzisothiazolyl)piperazinyl)butyl)-phenyl)-2-methylthiazole To a 100 ml round-bottomed flask equipped with condenser and $N_2$ inlet were added 1.43 g (4.11 mmol) 4-(4-chlorobutyl)phenyl)-2-methylthiazole hydrobromide, 0.90 g. (4.11 mmol) N-benzisothiazolylpiperazine, 0.72 g (4.11 mmol) diisopropylethyl amine, 0.87 g (8.22 mmol) sodium carbonate, 2 mg sodium iodide, and 40 ml methylisobutyl ketone. The reaction was refluxed 31 hours, cooled, filtered, and the filtrate evaporated. The residue was chromatographed on silica gel using ethyl acetate/methylene chloride as eluent to afford an oil, which was taken up in methylene chloride and precipitated by addition of ether saturated with HCl. The solid was filtered, washed with ether, dried briefly, then washed with a minimal amount of acetone and dried to afford a white solid, m.p. 207–212° C., 1.87 g (87.2%). NMR (DMSO-$d_6$): 1.6–1.8 (m, 4H), 2.64 (t, 2H), 2.72 (s, 3H), 3.1–3.3 (m, 4H), 3.4–3.6 (m, 4 H), 4.0 (d, 2H), 7.2–8.1 (m, 8H), 7.85 (s, 1H).

EXAMPLE 27
A. 4-(4-(4-Chlorobutyl)phenyl)-thiazol-2-one

To a 500 ml round-bottomed flask equipped with $N_2$ inlet were added 18 g (60 mmol) bromomethyl-(p-chlorobutyl)phenyl ketone, 5.76 g (60 mmol) potassium thiocyanate, and 150 ml acetone. The resulting reaction mixture rapidly deposited a white precipitate as it was stirred at room temperature for 3 hours. It was then filtered and the filtrate was evaporated to an oil. The oil was taken up in 100 ml boiling ethanol, and 50 ml 1N HCl was added very slowly so as to maintain a solution over 1.5 hours. Then 1 ml concentrated sulfuric acid was added and the reaction refluxed for 24 hours. The reaction mixture was cooled and decanted off a small amount of black oil into 1.2 l water. The aqueous mixture was stirred for 20 minutes, and the precipitate filtered, washed with water and hexane, and dried to a yellow solid, m.p. 111-117° C., 11.89 g (74.9%). NMR (CDCl$_3$) 1.79 (m, 4H), 2.64 (t,2H), 3.53 (t, 2H), 6.23 (d, 1H), 7.2-7.4 (m, 4H).

B.
4-(4-(4-(4-(3-Benzisothiazolyl)piperazinyl)butyl)-phenyl)-thiazol-2-one

To a 125 ml round-bottomed flask equipped with condenser and N$_2$inlet were added 1.10 g (4.11 mmol) 4-(4-(4-chlorobutyl)phenyl)-thiazol-2-one, 0.90 g (4.11 mmol) N-(3-benzoisothiazolyl)piperazine, 0.87 g (8.22 mmol) sodium carbonate, 2 mg sodium iodide, and 40 ml methylisobutylketone. The reaction mixture was heated at reflux for 44 hours, cooled, filtered, and the filtrate was evaporated. The residue was chromatographed on silica gel using ethyl acetate as eluent, and the product fractions collected and evaporated. The residue was taken up in methylene chloride/methanol, treated with ether saturated with HCl, and evaporated. The resulting solid was triturated with acetone to afford 1.10 g (55%) of white solid, m.p. 140-145° C. NMR (DMSO-d$_6$): 1.6-1.8 (m, 4H), 2.62 (t, 2H), 3.1-3.3 (m, 4H), 3.4-3.6 (m, 4H), 4.0-4.1 (m, 2H), 6.75 (d, 1H), 7.2-8.1 (m, 8H).

I claim:
1. A compound of the formula:

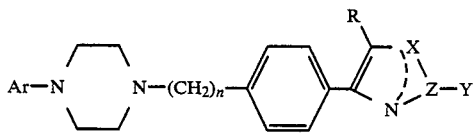

or a pharmaceutically acceptable acid addition salt thereof, wherein

Ar is phenyl or 3-trifluoromethylphenyl; 3-cyanopyridyl; naphthyl; or a heterocyclic ring selected from the group consisting of furyl; pyrrolyl; pyrazolyl; imidazolyl; oxazolyl; thiazolyl; isothiazolyl; pyridyl, and pyrimidyl; or a benzoheterocyclic ring selected from the group consisting of quinolyl; quinazolinyl; benzoxazolyl; benzimidazolyl; benzothiazolyl; and benzisothiazolyl; each of said naphthyl, heterocyclic ring or benzoheterocyclic ring optionally substituted by one fluoro, chloro or trifluoromethyl, said substitution in the case of said naphthyl or benzoheterocyclic ring being in the ring not attached to the piperazinyl group;

n is 2, 3 or 4;

R is hydrogen or (C$_1$-C$_3$) alkyl;

X is nitrogen, oxygen or sulfur, and

Z-Y is C-H, C-OH, C-SH, C-NH$_2$, C-(C$_1$-C$_3$) alkyl, C-(C$_1$-C$_3$) alkylamino or N, with the proviso that when Z-Y is nitrogen then X is not oxygen.

2. A compound according to claim 1 wherein n is 2 and R is hydrogen.

3. A compound according to claim 1 wherein n is 2 or 4 and Ar is naphthyl.

4. A compound according to claim 1 wherein X is sulfur, and Y is amino.

5. A compound according to claim 1 wherein n is 2 or 4 and Ar is a benzoheterocyclic ring selected from the group consisting of quinolyl; quinazolinyl; benzoxazolyl; benzimidazolyl; benzothiazolyl; and benzisothiazolyl.

6. A compound according to claim 5 wherein said benzo in said benzoheterocyclic ring is substituted by one of fluoro, chloro or trifluoromethyl.

7. A pharmaceutical composition comprising a compound according to claim 1 in an amount effective for removing or ameliorating the symptoms of psychotic schizophrenia, and a pharmaceutically acceptable carrier or diluent.

8. A composition according to claim 7 wherein n is 2 and R is hydrogen.

9. A composition according to claim 7 wherein n is 2 or 4 and Ar is naphthyl.

10. A composition according to claim 7 wherein X is sulfur, and Y is amino.

11. A composition according to claim 7 wherein n is 2 or 4 and Ar is a benzoheterocyclic ring selected from the group consisting of quinolyl; quinazolinyl; benzoxazolyl; benzimidazolyl; benzothiazolyl; and benzisothiazolyl.

12. A composition according to claim 11 wherein said benzo in said benzoheterocyclic ring is substituted by one of fluoro, chloro or trifluoromethyl.

13. A method for removing or ameliorating the symptoms of psychotic schizophrenia which comprises administering to a psychotic schizophrenic subject an effective amount of a compound according to claim 1.

* * * * *